US005114855A

United States Patent [19]
Hu et al.

[11] Patent Number: 5,114,855
[45] Date of Patent: May 19, 1992

[54] METHOD FOR AGGREGATING CELLS WITH SMALL MICROSPHERES

[75] Inventors: Wei-Shou Hu, Falcon Heights, Minn.; Stephane Goetghebeur, Villeneuve d'Ascq, France

[73] Assignee: Regents of the University of Minnesota, St. Paul, Minn.

[21] Appl. No.: 511,419

[22] Filed: Apr. 19, 1990

[51] Int. Cl.$^5$ .................. C12N 5/00; C12N 5/02; C12N 11/00

[52] U.S. Cl. .................. 435/240.24; 435/240.25; 435/174; 435/176; 435/177; 435/178; 435/180

[58] Field of Search ............. 435/240.1, 240.2, 240.23, 435/240.24, 240.25, 174, 176, 177, 178, 180

[56] References Cited

U.S. PATENT DOCUMENTS 4,266,032 5/1981 Miller et al.

OTHER PUBLICATIONS

H. Kubota, Cell Culture Using Microcarrier: The Effects of Chemical and Physical Properties of Microcarrier on Cell Attachment, Spreading and Growth (JAACT Meeting).

Hu, W. S. & Wang, D. I. C. (1987) Biotechnology & Bioengineering 30:548-557.

Kubota, H. & Nagaike (1989) Abstract, Japanese Assn of Animal Cell Technology Annual Meeting, Tsukuba City, Japan Nov. 20-22, 1989.

Fiorentine, D., Shahar, A. and Mizrahi, A. (1985), Production of Herpesvirrus of Turkeys In Microcarrier Culturing System—A New Method For Production of Vaccine Against Marek's Disease, Develp. Biol. Standard 60:421–430.

Lazar, A., Silverstein, L. and Mizahri, A. (1985), Agarose-Polyacrolein Microsphere Beads: A new Microcarrier Culturing System, Develop. Biol. Standard, 60:457-465.

Kotler, M., Reuveny, S., Mizrah, A. and Shahar, A. (1985), Ion Exchange Capacity of DEAE Microcarriers Determined The Growth Pattern of Cells In culture, Develop. Biol. Standard, 60:225-261.

Avgerinos, G. C., Drapeau, D., Socolow, J. S., Mao, J., Hsiao, K., Broeze, R. J. (1990), Spin Filter Perfusion System For High Density Cell Culture-Production of Recombinant Urinary Type Plasminogen Activator In CHO Cells, Biotechnology 8:54–57.

SoloHill Engineering, Inc. (U.S.A. 1985), Bioglas Microcarrier Beads Price List and Promotional Materials (4 pages).

Percell Biolytical (Sweden, 1988), Technical Bulletin regarding Cultispher-G Macroporous Gelatin Microcarrier (4 pages).

Tung, A. S., Sample, J. vG., Brown, T. A., Ray, N. G., Hayman, E. G. and Runstadler, P. R. Jr. (1988), TPA Production Through Mass Culturing of Chinese Hamster Ovary Cells, Biopharm Manufacturing reprint.

Litwin, J. (1985), The Growth Of Human Diploid Fibroblasts As Aggregages With Cellulose Fibres In Suspension, Develop. Biol. Standard, 60:237-242.

Avgerinos, G. C., and Drapeau, D. (1988) Production Scale Mammalian Cell Suspension Perfusion Culture With A Rotating Wire Mesh Screen, abstract and presentation at the Engineering Foundation on Cell Culture Engineering, Palm Coast, Fla., U.S.A., Jan. 31—Feb. 5, 1988.

(List continued on next page.)

Primary Examiner—David M. Naff
Assistant Examiner—Jane Williams
Attorney, Agent, or Firm—Faegre & Benson; Kakare, S. B., Phillips, P. G., Burke, D. H. and Dean, R. C., Jr. (1985), Continuous Production of Monoclonal Antibodies by Chemostatic and Immobulized Hybridoma Culture, in Large Scale Mammalian Cell Culture Technology, A. S. Lubnoicky Ed. 127-149.

[57] ABSTRACT

A method of inducing aggregate formation of animal cells is carried out by forming a nutrient medium suspension of animal cells and introducing itno the suspension microspheres of a derivatized diameter of not more than about 60 μm, when measured in a suitable buffer saline or cell culture media.

46 Claims, 8 Drawing Sheets

OTHER PUBLICATIONS

Kakare, S. B., Webster, J., and Tajiri, D. (1988), Modeling Of Continuous Culture of "Clumped" CHO Cells For The Production of Erythropoietin, abstract and presentation at the Engineering Foundation on Cell Culture Engineering, Palm Coast, Fla., U.S.A., Jan. 31–Feb. 5, 1988.

Reuveny, S. (N.Y., U.S.A. 1983), Microcarriers For Culturing Mammalian Cells And Their Applications, Advances in Biotechnological Processes 2, pp. 1–32.

Ventrex Laboratories, Inc. (Me., U.S.A. 1986), Promotional Materials for Ventreglas ® glass beads.

Hu, W. S. and Wang, D. I. C. (1986), "Mammalian Cell Culture Technology: A Review From An Engineering Perspective," in Mammalian Cell Technology, Ed. W. G. Thilly, Butterworths Publishing Company pp. 167–197.

van Wezel, A. L. (1967), Growth of Cell-strains and Primary Cells on Micro-carriers in Homogenous Culture, Nature 216:64–65.

Johansson A. and Nielsen, V. (1980), Biosilon ® A New Microcarrier, Develop. Biol. Standard, 46:125–129.

Kuo, M. J., Lewis, C. Jr., Martin, R. A., Miller, R. E. Schoenfeld, R. A., Schuck, J. M. and Wildi, B. S. (1981), Growth of Anchorage Dependent Mammalian Cells on Glycine-Derivatized Polystyrene in Suspension Culture, in vitro, vol. 17, No. 10, pp. 901–906.

Reuveny, S., Silberstein, L., Shahar, A., Freeman, E., and Mizrahi, A. (1982), Cell and Virus Propagation on Cylindrical Cellulose Based Microcarriers, Develop. Biol. Standard, 50:115–123.

Knazek, R. A., Gullino, P. M., Kohler, P. O., and Dedrick, R. L. (1972) Cell Culture on Artificial Capillaries: An Approach to Tissue Growth in vitro, Science 178:65–67.

Lydersen, B. K., Pugh, G. G., Paris, M. S., Sharma, B. P., Noll, L. A. (1985), Ceramic Matrix for Large Scale Animal Cell Culture, Biotechnical, Jan. 1985:63–67.

Hu, W. S., Meier, J., Wang, D. I. C. (1985), A Mechanistic Analysis of the Inoculum Requirement for the Cultivation of Mammalian Cells on Microcarriers, Biotechnology and Bioengineering 27:585–595.

Varni, J., Dame, J., Rediske, J., Beals, T. F., Hillegas, W. (1985), Substrate-Dependent Differences In Growth And Biological Properties of Fibroblasts And Epithelial Cells Grown In Microcarrier Culture, Journal of Biological Standardization 13:67–76.

Fisher, P. E. and Tickle, C. (1981), Differences In Alignment Of Normal And Transformed Cells On Glass Fibres, Exp. Cell Res. 131:Res. 131:407–410.

Tolbert, W. R., Hitt, M. M. and Feder, J. (1980), Cell Aggregate Suspension Culture For Large-Scale Production Of Biomolecules, in vitro 16(6):486–490.

Levine, D. W., Wang, D. I. C. and Thilly, W. G. (1979), Optimization of Growth Surface Parameters In Microcarrier Cell Culture, Biotechnology and Bioengineering 21:821–845.

Hu, W. S. and Dodge, T. C. (1985), Cultivation of Mammalian Cells in Bioreactors, Biotechnology Progress 1:209–215.

Blasey, H. D., Grossebueter, W., Lehman, J., Giehring, H. and Schwengers, D. (1988), B-interferon Production In Serum-free Medium on a New Type of Microcarrier, presentation at the Engineering Foundation on Cell Culture Engineering, Palm Coast, Fla., U.S.A., Jan. 31–Feb. 5, 1988.

Murata, M., Eto, Y. and Shibai, H. (1988), Large-scale Production of Erythroid Differentiation Factor By Gene-engineered Chinese Hamster Ovary (CHO) Cells In Suspension Culture, J. Ferment. Technol. 66:501–507.

CHO CELLS CULTIVATED IN SUSPENSION

SIZE DISTRIBUTION OF CHO CELLS AGGREGATES

MICROSPHERE INDUCED AGGREGATE CULTURE OF 293 CELLS

MICROSPHERE INDUCED AGGREGATE CULTURE OF NL ST CELLS

METHOD FOR AGGREGATING CELLS WITH SMALL MICROSPHERES

FIELD OF THE INVENTION

This invention relates to a method for aggregating and cultivating anchorage-dependent cells, surface-grown cells and suspension-grown cells in a microsphere-induced aggregate culture. More specifically, the invention relates to the surprising discovery that by introducing microspheres of a derivatized diameter of less than about 60 μm, when measured in a suitable buffer saline or cell culture media, into a nutrient medium including such cells, very high cell concentrations can be achieved over a longer range of time with a much lower microsphere concentration than has been possible with the previous use of much larger microspheres having a hydrated diameter of approximately 100 to 400 μm.

BACKGROUND OF THE INVENTION

Many animal cells used for the production of viral vaccines, growth factors, receptors or therapeutic proteins are anchorage-dependent, i.e. they must adhere to a compatible surface in order to grow. This requirement is particularly stringent for normal diploid cells; these cells not only need to attach to a surface, they develop a polarized, elongated cell shape after attachment and eventually grow to cover the surface and reach a state of confluence. At confluence cell division stops. Contact-inhibition stays further cell growth. These cells form a monolayer of cells on a surface. Cell growth resumes only after the cells are detached by exposure to a proteolytic agent, such as trypsin, and plated onto a larger surface.

Transformed cells and continuous (non-diploid) cell lines, on the other hand, often retain the requirement of surface for growth but lose the characteristic of contact inhibition. Such cells may form multiple layers of cells on a surface if proper growth medium is available. (See Hu, W-S. and Dodge, T. C. (1985), "Cultivation of Mammalian Cells In Bioreactors", *Biotechnol. Prog.* 1, 209–215). Although some transformed cells acquire the ability to grow in suspension, many of these cells preferentially adhere to a surface if a compatible surface is available.

Conventionally, cells have been cultivated in roller bottles. Since the 1980's, the demand for large quantities of therapeutic proteins, such as tissue type plasminogen activator, has resulted in a wider application of many alternative cultivation methods which are more suitable for large-scale operations. These alternative methods include microcarriers based on dextran (See Van Wezel, A. L. (1967), "Growth of Cell Strains and Primary Cells on Microcarriers in Homogenous Culture", *Nature* 216:64:65); polystyrene (See Johansson, A. and Nielsen, V. (1980), "Biosilon: A New Microcarrier", *Dev. Biol. Stand* 46:125–129 and Kuo, M. J., Lewis, C. Jr., Martin, R. A., Miller, R. E., Schoenfeld, R. A., Scheck, J. M. and Wildi, B. S. (1981), "Growth of Anchorage-Dependent Mammalian Cells on Glycine-Derivatized Polystyrene in Suspension Culture", *In Vitro* 17:901–906); cellulose (See Reuveny, S., Silberstein, L., Shahar, A., Freeman, E. and Mizrahi, A. (1982), "Cell and Virus Propagation on Cylindrical Cellulose Based Microcarriers", *Dev. Biol. Stand.* 50:115–123); collagen (See R. C. Dean et al. (1985), *Large Scale Mammalian Cell Culture Technology.* Ed. B. K. Lydersen, Hansen Publishers, New York, N.Y., pp. 145–167); gelatin-based macroporous beads (See *Cultisphere, Technical Bulletin*, Percell Biolytica AB); hollow-fiber bioreactors (See Knazek, R. A., Gullino, P. M., Kohler, P. O. and Dedrick, R. L. (1972), *Science* 178:65); and ceramic bioreactors (See Lydersen, B. K., Pugh, C. G., Paris, M. S., Sharma, B. P. and Noll, L. A. (1985), *Biotechnology* 3:63).

Among these techniques, microcarrier technology is the most widely employed, especially in vaccine production. The mean diameter of microcarriers reported in the literature are generally in the range of 130 μm to 200 μm. (See, e.g., Hu, W-S., Meier, J. and Wang, D. I. C. (1985), "A Mechanistic Analysis of The Inoculum Requirement For The Cultivation of Mammalian Cells on Microcarriers"; *Biotechnol. Bioeng.* 27, 585–595; Varani, J., Dame, M., Fediske, J., Beals, T. F. and Hillegas, W. (1985), "Substrate-Dependent Differences in Growth and Biological Properties of Fibroblasts And Epithelial Cells Grown in Microcarrier Culture", *J. Biol. Stand.* 13:67–76; *Microcarrier Culture*, Pharmacia Fine Chemicals Technical Bulletin; Blasey, H. D., Grossebueter, W., Lehman, J., Giehring, H. and Schwengers, D. (1988), "B-interferon Production in Serum-Free Medium On A New Type Of Microcarrier", Presentation at the Engineering Foundation on Cell Culture Engineering, Palm Coast, FL, U.S.A., Jan. 31–Feb. 5, 1988.). However, a range as wide as from 100 to 400 μm has been said to be suitable for growth. (See, e.g., Butler, M. (1987), "Growth Limitation In Microcarrier Culture", *Adv. Biochemical Engineering/Biotechnology* 34:57–84.). It should be noted that the diameter of many types of microcarriers change with the ionic strength and pH of the solution in which they are suspended. In this patent application, the diameter measured in a phosphate buffer saline or cell culture media will be referred to as the hydrated diameter.

Because most types of microcarriers have an apparent density slightly heavier than water (1.02–1 g/cm$^3$), a conventional stirred-tank, or fermentor, is used to keep microcarriers in suspension. Once suspended, cells attach, spread and grow on the external surface of the microcarriers. The concentration of microcarriers used generally ranges from an equivalent of 2% of the settled bead volume to 12% of the settled bead volume. Although as high as 40% of settled bead volume has been used, it is not common practice. (See Hu, W-S., Meier, J. and Wang, D. I. C. (1985), "A Mechanistic Analysis of The Inoculum Requirement For The Cultivation of Mammalian Cells on Microcarriers", *Biotechnol. Bioeng.* 27, 585–595.).

A major advantage of microcarrier technology is the large amount of available cell growth area (0.4 m$^2$/l to 3 m$^2$/l) that can be contained in the reactor vessel. A drawback of microcarrier technology, on the other hand, is the large amount of settled bead volume per unit volume of the reactor. Virtually all this volume is inert; except for providing growth surface, the settled bead volume is not contributing to cell growth and product formation. The relatively large amount of settled bead volume also increases the degree of sophistication required for the design of an agitation system to suspend the beads without damaging the cells. (See Hu, W-S. and Wang, D. I. C. (1986) "Mammalian Cell Culture Technology: A Review From An Engineering Perspective", *Mammalian Cell Technology*. Ed. W. G. Thilly, Butterworths Publishing Company.).

In principle, it might appear that the diameter of microcarriers could be decreased to increase the cell growth surface area per unit volume of microcarriers. The external surface per unit volume of microcarriers increases linearly with decreasing diameter. Furthermore, it has been proposed that smaller beads have a lower frequency of collision and a lower kinetic energy, and may reduce possible collision damage of cells in a bioreactor. (See Cherry, R. S. and Papoutsakis, E. T. (1986) "Hydrodynamic Effects On Cells In Agitated Tissue Culture Reactor" (Bioprocess Eng. 1:29-41)).

Despite the possible benefits of smaller microcarrier beads published reports state that the minimum optimal diameter range for the selected microcarrier is between 90–100 μm. It has ben speculated that it is a disadvantage to have cells adhere to a more curved surface such as the surface available on smaller diameter beads. (Id.). This belief is consistent with a previous report on cell growth on glass fiber which appears to indicate that curvature of surface plays a role in how cells grow.

As a result of these findings, the diameter range of commercially available microcarriers fall in the range of the reported "optimal" diameter range of 90–200 μm. (See Hu, W-S. and Wang, D. I. C. (1987), "Selection of Microcarrier Diameter For The Cultivation of Mammalian Cells on Microcarriers", *Biotechnol. Bioeng.* 30, 548–555; Kubota, H. and Nagaike, K. (1989), "Cell Culture Using Microcarriers: The Effect of Chemical And Physical Properties of Microcarrier on Cell Attachment, Spreading and Growth", Abstract and presentation at the Japanese Association of Animal Cell Technology annual meeting, Tsukuba City, Japan, Nov. 20–22, 1989.).

Similarly, chick fibroblasts cultivated on glass wool fibers have been observed to spread along different directions on the fiber if the fiber diameter is larger than 100 μm. When cultivated on fibers of about 70 μm, they spread and grow only along the longitudinal direction. (See Fisher, P. E. and Tickle, C. (1981), "Differences in Alignment Of Normal and Transformed Cells on Glass Fibers", *Exp. Cell Res.* 131:407:410.).

Furthermore, cells attached to small beads do not develop their typical morphology as they do on a flat surface. Exceptions to the aforementioned optimum diameter range do exist. For example, when celluloid materials were used, such as DE-52 and DE-53, the diameter of rods was approximately 40 μm or longer, up to hundreds of μm. (See Reuveny, supra). In another case, small polystyrene beads BioBeads SX-1 of 25 μm were used. These beads failed to support significant cell growth (only 60% increase in DNA content over a 14-day period). However, other polystyrene beads of unspecified diameter and only after some surface modifications, did support cell growth.

To circumvent the drawbacks of microcarriers, some have opted to use cells which can be adapted to grow in suspension. Chinese hamster ovary (CHO) cells can be used in this fashion. (See Murata, M., Eto, Y. and Shibai, H. (1988), "Large-Scale Production of Erythroid Differentiation Factory By Gene-Engineered Chinese Hamster Ovary (CHO) Cells in Suspension Culture", *J. Ferment. Technol.* 66:501–507.). However, the use of suspension cells suffers another shortcoming: the maximum cell concentration achievable in a conventional stirred-tank bioreactor is only in the vicinity of $2 \times 10^6$/ml. To achieve a high cell concentration, the medium has to be replenished intermittently or perfused continuously to supply nutrients and to remove metabolites. In a microcarrier culture, on the other hand, cells on microcarriers can be retained in the bioreactor by sedimentation or by withdrawing the medium through a rotating sieve. In a suspension culture, cell retention in the bioreactor poses some difficulty, and continuous or intermittent medium replenishment inevitably removes cells along with the spent medium.

An approach recently adopted to overcome this problem is to cultivate some transformed cells as cell aggregates. (See Tolbert, W., Hitt, and Feder, J. (1980), "Cell Aggregate Suspension Culture", *In Vitro* 16:486:490.). Different methods have been used to induce the aggregate formation for cells which normally grow on surface or prefer to grow on surface. This method usually involves the use of medium containing a low concentration of calcium in conjunction with a moderately high agitation rate. The aggregate method of cell cultivation allows for easier cell retention due to the larger size of the particles. Thus, a high cell concentration can potentially be achieved. Compared with a microcarrier culture, the settled volume of the solid phase (cell mass or beads) is much lower than the same cell concentration in an aggregate culture.

The sizes of cell aggregates span widely from single cells to very large aggregates of hundreds of μm in diameter. It is believed that throughout the cultivation period single cells and small aggregates continuously adhere to one another to form new or larger aggregates, while larger aggregates continuously break down to generate smaller ones. With such a wide range of aggregate size, the cultivation conditions using simple suspension culture techniques are hardly optimum. Large aggregates, as large as 1 mm, may suffer nutrient transfer limitations in their interiors, while small aggregates may easily be washed out in a continuous flow reactor. Therefore, it is not surprising that despite its high total cell concentration the increase in volumetric productivity of an aggregate culture is often not proportional to the increase in cell concentration from that of a conventional continuous flow reactor.

Furthermore, only cells which are capable of growing in suspension, such as CHO cells (See Karkare, S. B., Webster, J. and Tajiri, D. (1988), "Modeling of Continuous Culture of Clumped CHO Cells For the Production of Erythroprotein", Abstract and Presentation at the Engineering Foundation on Cell Culture Engineering, Palm Coast, FL, U.S.A., January 31-February 5, 1988); or highly transformed cells such as CRL 598 cells (See Avgerinos, G. C. and Drapeau, D. (1988), "Production Scale Mammalian Cell Suspension Perfusion Culture With a Rotating Wire Mesh Screen", Abstract and presentation at the Engineering Foundation on Cell Culture Engineering, Palm Coast, Fla., U.S.A., Jan. 31–Feb. 5, 1988); can be grown in aggregate form in a suspension culture.

Conventional microcarriers have also been used to generate cell clumps or aggregates. In the study described by G. C. Avgerinos, D. Drapeau, J. S. Socolow, J. I. Mao, K. Hsiao and R. J. Broeze, "Spin Filter Perfusion System For High Density Cell Culture: Production Of Recombinant Urinary Type Plasminogen Activator In CHO Cells", *Bio/Technology* 8:54–58, Chinese hamster ovary cells were cultivated in conventional microcarriers (Cytodex 2, Pharmacia) and grow normally. After the cells reached confluence, the cells began to migrate toward one end of the microcarriers and began to form clumps. After 18 days, some large aggregates with diameters in the range of 200 to 600 μm were observed.

Similarly, in other studies, it has been reported that certain cells cultivated on cellulose rods formed aggregates which contained a number of cellulose rods and cells bridged between these rods. (See J. Litwin, "The Growth Of Human Diploid Fibroblasts As Aggregates With Cellulose Fibers In Suspension", *Dev. Biol. Standard.* 60:237-242 (1985) and Kotler, M. Reuveny, S., Misrahi, A. and Shahaz, A, "Ion Exchange Capacity Of DEAE-Microcarriers Determined The Growth Pattern Of Cells In Culture", *Dev. Biol. Standard.* 60:255-261 (1985).). In these studies, using conventional microcarriers (Cytodex 2 and cellulose), a large amount of microcarrier was used.

BRIEF DESCRIPTION OF THE INVENTION

This invention provides a method of inducing aggregate formation of animal cells by forming a suspension of animal cells in nutrient medium and introducing microspheres of a derivatized diameter of not more than about 60 μm, when measured in a suitable buffer saline or cell culture media, into the suspension. These cells may be anchorage-dependent cells, cells which grow in suspension or cells which grow on a surface.

DETAILED DESCRIPTION OF THE INVENTION

Figure 1:
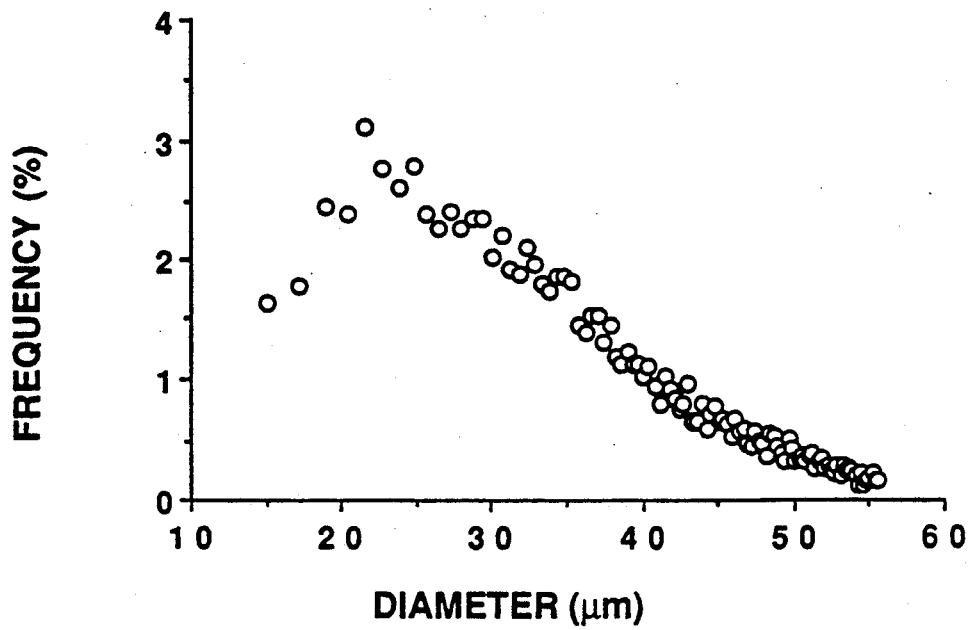
FIG. 1 a graph of size distribution of microspheres used in the present invention.

Our invention is the use of microspheres of an unexpectedly small hydrated derivatized diameter of less than about 60 μm to induce aggregate formation for anchorage-dependent cells, cells which grow in suspension or cells which grow on a surface. This methodology is analogous to the seeding of nuclei in a crystallization process in which small crystals are added to a saturated solution to induce crystal growth. The microspheres added to the cell suspension allow cells to attach to the surface preferentially than to each other. The aggregate is formed by the outgrowth of cells on the microspheres and/or by agglomeration of a number of microspheres.

Many materials, essentially any one which allows a rapid cell attachment, can be used for the microspheres. Examples of suitable microsphere materials for use in the present invention are (i) cross-linked dextran beads (such as Sephadex) with chemical derivatization as described in Levine et al. Biotechnol. Bioeng. (1979) 21:821-845 with gelatin or collagen coating as prepared similarly to Cytodex 3 (Pharmacia, Sweden); (ii) gelatin; (iii) polyacrylamide-copolymerized with collagen or gelatin, (iv) polyacrylamide with modified charge; (v) polystyrene, preferably with chemical modification to attach charged group or collagen or gelatin to its surface; or (vi) glass, preferably hollow glass beads to adjust the density t the vicinity of 1.00 g/cm$^3$.

The selection of the microsphere diameter is dictated by certain constraints. First, each microsphere or bead should have enough cells to initiate growth. In other words, the mean of cells/bead at the initiation of the culture should be sufficiently high, so that the fraction of beads with no cells is minimum. Assuming a Poisson distribution, the desired mean is approximately 4 to 5 cells/bead.

Second, to allow for a high efficiency of cell attachment, ample surface area should be available initially so that the rate of cell attachment is not limited by surface area. In other words, the rate of cell attachment to the surface should exhibit zero order kinetics with respect to surface area. This can be true only if sufficient surface is still available after initial cell attachment. Therefore, the microsphere should be able to accommodate a monolayer cell density in the range of 10-20 cells/bead. Most continuous cell lines of interest in bioprocessing have a diameter of 10-20 μm. Cells can be assumed to be spheres of identical diameter as a first approximation. If one uses microspheres of the same diameter as cells, cells can be adhered to each microsphere in a close-packed face-center pattern. Thus, in principle, microspheres of 10-20 μm can be employed as aggregate inducers. Taking into account that cells are not perfect spheres and that their diameters are not uniform, one may employ slightly larger beads, of no more than about 60 μm diameter. In any case, smaller beads are preferred, so that all the surface can be quickly covered by cells after a very short time of cultivation to allow for cell outgrowth and aggregate formation. Furthermore, because the beads used are small, the volume fraction they occupy in a bioreactor is very small.

Preparation of Microspheres

Sephadex G25-50 microspheres or beads were purchased from Sigma Chemical Co., Mo. These beads are cross-linked dextran beads with an unhydrated diameter range approximately between 25–50 μm. The beads are used in gel filtration and do not support cell growth or attachment. To facilitate cell growth and attachment, the beads were derivatized with Diethylaminoethyl-chloride-hydroxychloride (DEAE Cl HCl) (Sigma) according to the procedure set forth in Hu, W-S., Meier, J. and Wang, D. I. C. (1985), "A Mechanistic Analysis of The Inoculum Requirement For The Cultivation of Mammalian Cells on Microcarriers", *Biotechnol. Bioeng.* 27, 585-595; and Levine, D. W., Wang, D. I. C. and Thilly, W. G. (1979), "Optimization of Growth Surface Parameters in Microcarrier Cell Culture", *Biotechnol. Bioeng.* 21:821-845.

Briefly, 1 g Sephadex G25-50 in 12 ml distilled water and 6 ml of 2.0 M DEAE Cl HCl were poured into a 250 ml round bottom flask. The flask was rotated in a water-bath kept at a constant temperature of 60° C. 12 ml of 3.0 M NaOH was warmed up in a separate flask. After 30 min, the reaction was started by adding the prewarmed NaOH to the bead suspension. The reaction was carried out for 40 min and then quenched by the addition of 200 ml distilled water. The beads were then poured into a siliconized 150 ml sintered glass funnel and washed with 500 ml water, 300 ml 0.1 N HCl, 500 ml 0.0001 N HCl, 200 ml water and 400 ml phosophate buffer saline (PBS) in the above order. The beads were then resuspended in 100 ml PBS, autoclaved, and stored as a stock suspension until use.

The size distribution of the beads after derivatization was determined using a Coulter channelyzer model C1000 attached to a Coulter counter model ZB (Coulter Electronics, Hialeach, FL) with a 200 μm aperture tube coupled to a channelizer. 2 ml of 10 g/l Sephadex G25-50 stock suspension were diluted in 80 ml Isoton 2. FIG. 1 shows the diameter distribution of the resulting microspheres. The median diameter is 23 μm while the mean diameter is about 32 μm.

EXAMPLE 1

Cultivation of Chinese Hamster Ovary (CHO) Cells in Microsphere-Induced Aggregate Culture CHO cells were obtained from D. Giard of the Cell Culture Center, Massachusetts Institute of Technology, Cambridge, MA. Confluent CHO cells on a T-75 flask (Corning Glass, Corning, NY) were detached by exposure to a 0.25% trypsin (Gibco Laboratories, Grand Island, N.Y.) in PBS for 5 min. The detached cells were resuspended in the growth medium for inoculation into subsequent cultures. 0.5 g/l of microspheres prepared as described above were used in this experiment. For comparison, a simple suspension culture (CHO cells can grow in suspension) was also included. The growth medium was a mixture of Dulbecco's Modified Eagle's Medium (DMEM) and Ham's F-12 medium (F12) at 3:1 ratio (DMEM/F12 3:1) supplemented with 2.5% (v/v) of fetal bovine serum (FBS) (Hyclone Laboratories, Inc., Logan, UT). The experiment was carried out in 250 ml spinner flasks with a suspended magnetic stirring bar (Wilbur Scientific Co., Boston, MA). The CHO cells were inoculated into spinners while they were agitated continuously. The agitation rate used was 65 rpm and 55 rpm for the microsphere and suspension cultures, respectively. A slightly higher agitation rate was used in the microsphere culture to avoid any possible settling of large aggregates.

Figure 2:
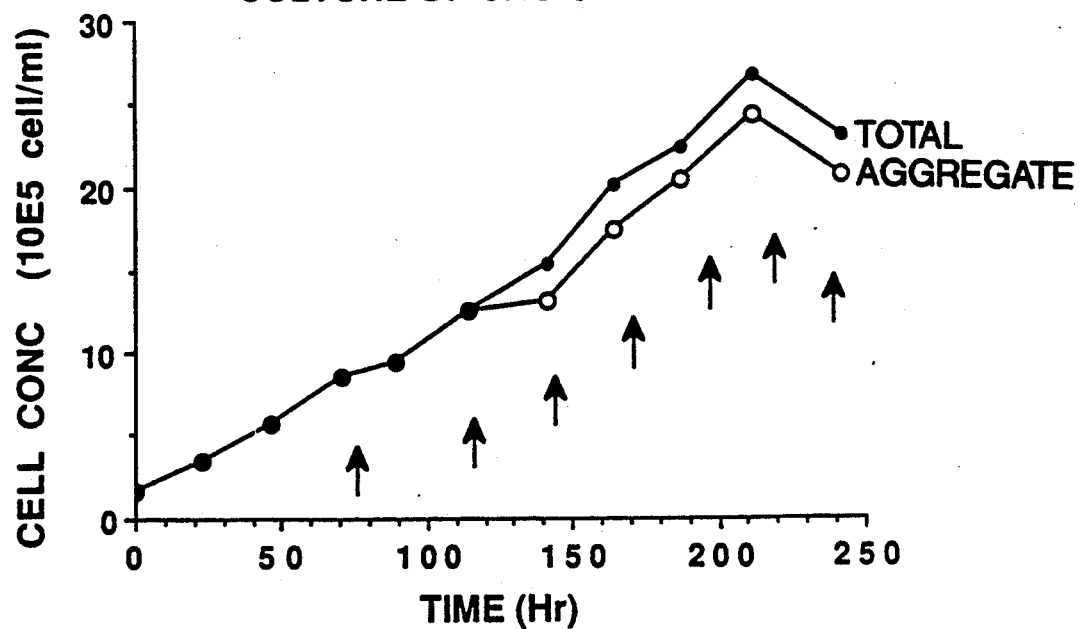
FIG. 2 is a graph of cell concentration vs. time for microsphere induced aggregate culture of CHO cells according to the present invention.
Figure 3:
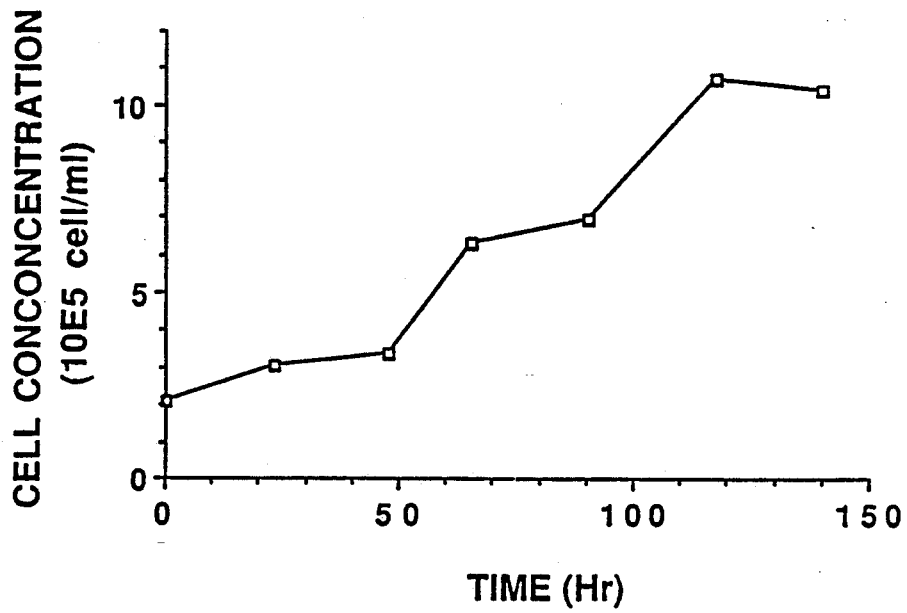
FIG. 3 is a graph of cell concentration vs. time for CHO cells cultivated in suspension according to the present invention.

The growth kinetics of both cultures are shown in FIGS. 2 and 3. In both cultures, cell concentration began to increase after inoculation with a doubling time of approximately one day. The glucose concentration decreased during cell growth and the nutrient medium was withdrawn and replaced with fresh nutrient medium when the glucose concentration was low. In the case of the microsphere culture, the aggregates were allowed to settle and approximately 90% of the nutrient medium was replenished (as indicated by the arrows in FIG. 2). In the suspension culture without microspheres, the culture was withdrawn and transferred to a centrifuge tube at 75 h and 120 h. The cells were pelleted by centrifugation, and the spent medium was discarded and replaced with fresh medium; cells were then transferred back to the culture flask for further cultivation.

The growth rate in the suspension culture without microspheres decreased when the cell concentration approached $10^6$ cells/ml. In the suspension culture, a cell concentration of approximately $1.05 \times 10^6$ cells/ml was reached at 120 h. Nutrient medium replenishment was not practiced and the suspension culture was terminated at 147 h.

In the microsphere culture, aggregates were formed from the beginning; however, after 114 h some single cells and small aggregates (without the presence of microspheres) begin to appear in the suspension. Both the total cell concentration and the concentration of cells in microsphere-induced aggregates are shown in FIG. 2. The difference between total cell concentration and adherent cell concentration is the amount of cells growing in the suspension. The concentration of the cells continues to increase to more than $2.7 \times 10^6$ cells/ml at 210 h. In a typical microcarrier culture using Cytodex 1, the cell concentration achieved was approximately $1.5 \times 10^6$ cells/ml at 2 g/l of microcarriers. Cytodex 1 are DEAE derivatized dextran beads of 180 μm average diameter, available from Sigma Chemical Co., St. Louis, Mo.

Results from this experiment showed that after inoculation with the stock suspension of Sephadex G25-50 microspheres prepared as above, CHO cells adhered to the microspheres as single cells and cell aggregates began to form by agglomeration between cells adhered to different microspheres. 72 h after inoculation, all the cells grew in aggregate form with varying numbers of microspheres per aggregate. In the suspension culture without microspheres, small aggregates also formed.

Figure 4:
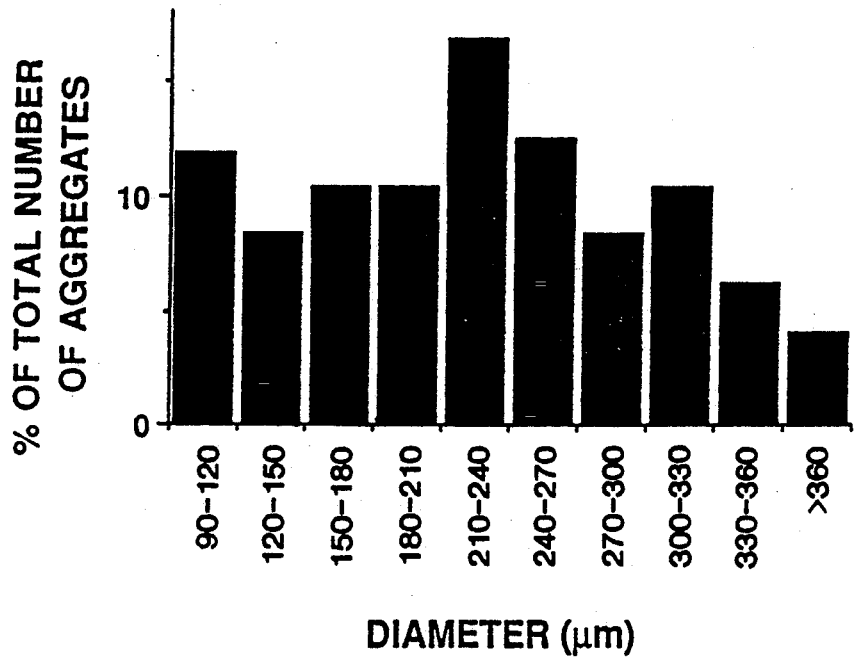
FIG. 4 is a histogram of size distribution of CHO cell aggregates.

A sample was taken from the suspension culture without microspheres at 150 h and from the microsphere-induced aggregates at 250 h for particle size distribution determination. To estimate the particle size distribution of the microsphere-induced aggregates, micrographs of these aggregates, shown in FIG. 6, were taken and the distances between the shortest two ends as well as the longest two ends were measured and the average was used as the characteristic diameter. The histogram of the diameter distribution is shown in FIG. 4. As can be seen, the aggregate diameter ranged from 90 μm to more than 360 μm with the majority of the aggregates having a diameter ranging from 90 to 330 μm. A small fraction of aggregates have a diameter as large as 500 μm.

Figure 5A:
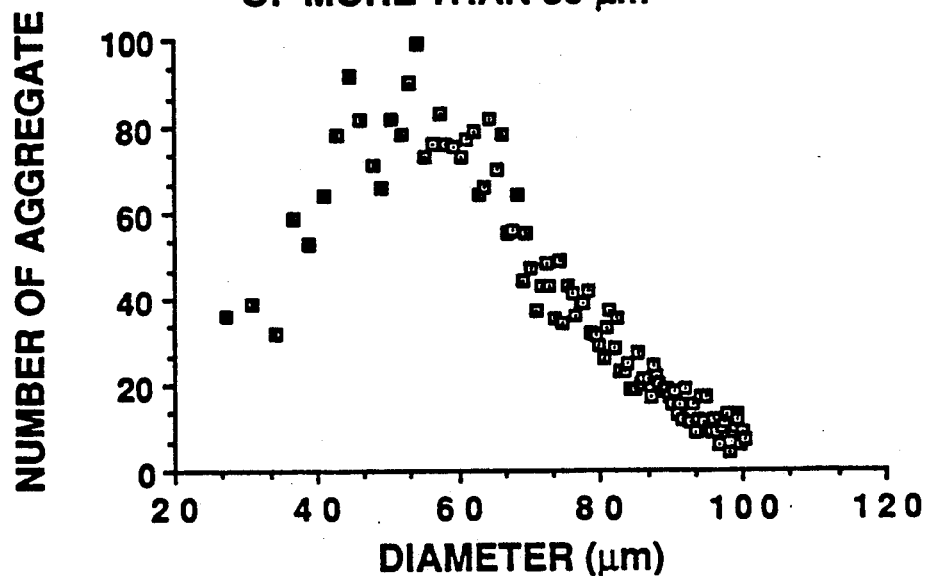
FIG. 5a represents the diameter distribution of aggregates of more than 30 μm in a suspension without the use of microspheres.
Figure 5B:
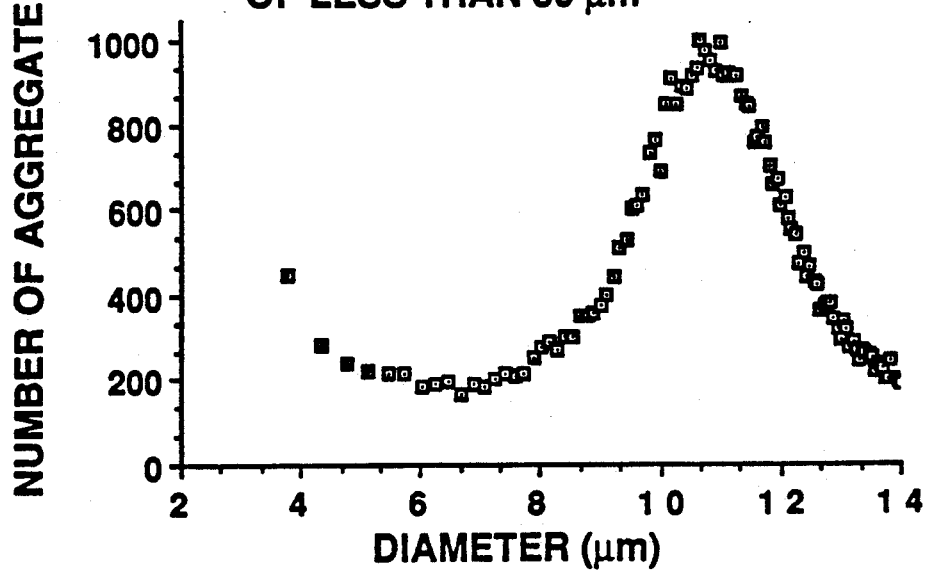
FIG. 5b represents the diameter distribution of aggregates of less than 30 μm in a suspension without the use of microspheres.

The aggregate diameter distribution of the suspension culture without microspheres was determined by passing the cell suspension through a sieve with an opening of 30 μm in diameter (FIG. 5). Approximately 98% of the cell particles have a diameter less than 30 μm. The mean diameter of this cell population was 11 μm. These results indicate that the cells are mostly single cells or small clumps of cells. On the other hand, the 2% cell population with a diameter greater than 30 μm were mostly aggregates up to tens of cells. The mean diameter of this aggregate cell population was approximately 55 μm.

Figure 6:
FIG. 6 is a micrograph of microsphere-induced CHO aggregates according to the present invention.

FIG. 6 shows microphotographs of microsphere-induced aggregates according to this Example. To determine the viability of the cells in these aggregates, samples were taken from the 250 h culture and were stained with fluorescein diacetate and ethidium bromide (FDA/EtBR) solution. The concentration of fluorescein diacetate and ethidium bromide were 5 μg/ml and 20 μg/ml, respectively. Using this staining method, dead cells exhibit orange color and the viable cells green color in a fluoresence microscope. As can be seen through the fluorescence microscope, most of the cells in the culture appeared to be viable even in the relatively large aggregates.

EXAMPLE 2

Cultivation of a Human Kidney Cell to Human Kidney Cell 293 in Microsphere-Aggregate Culture The human kidney cell, 293, used in this study has been genetically engineered to produce Protein C and was obtained from Lilly Research Laboratories, Indianapolis, Ind. The microspheres used were from the same stock suspension prepared as described above.

Figure 7:
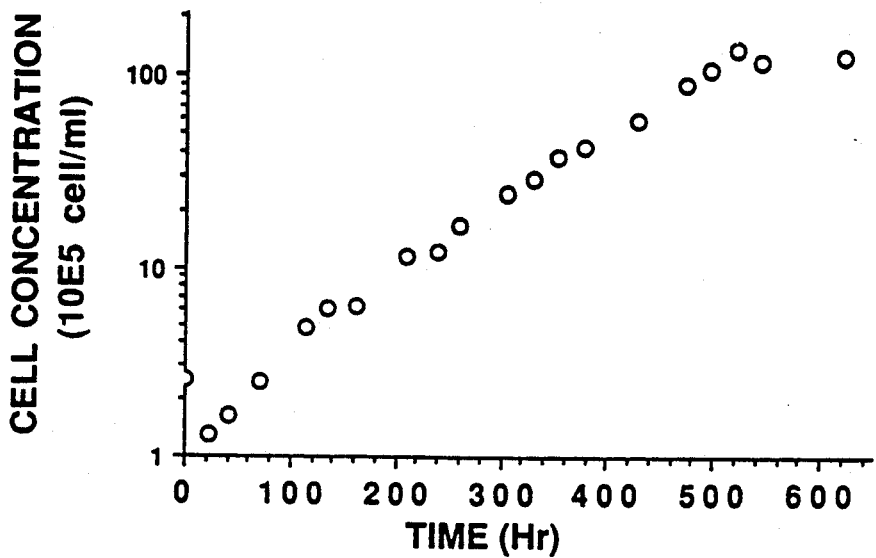
FIG. 7 is a graph of cell concentration vs. time for microsphere induced aggregate culture of human kidney 293 cells according to the present invention.

The growth medium used was DMEM/F12 3:1 supplemented with 2.5% FBS and 300 μg/ml geneticin and 200 μg/ml of hygromycin. 250 ml spinner flasks with 100 ml of microspheres at 0.5 g/l were used. The agitation rate was 80 rpm. Cells were inoculated with the stock suspension of microspheres prepared above at $2.5 \times 10^5$/ml. 293 cells are known to attach poorly to many types of microcarriers and only 60% of the cells inoculated attached to the microspheres. However, after attachment cells grew exponentially for a period of 500 h. The cell concentration reached $1.3 \times 10^7$ cells/ml at 500 h and remained relatively constant during the rest of the cultivation time (FIG. 7).

Figure 8:
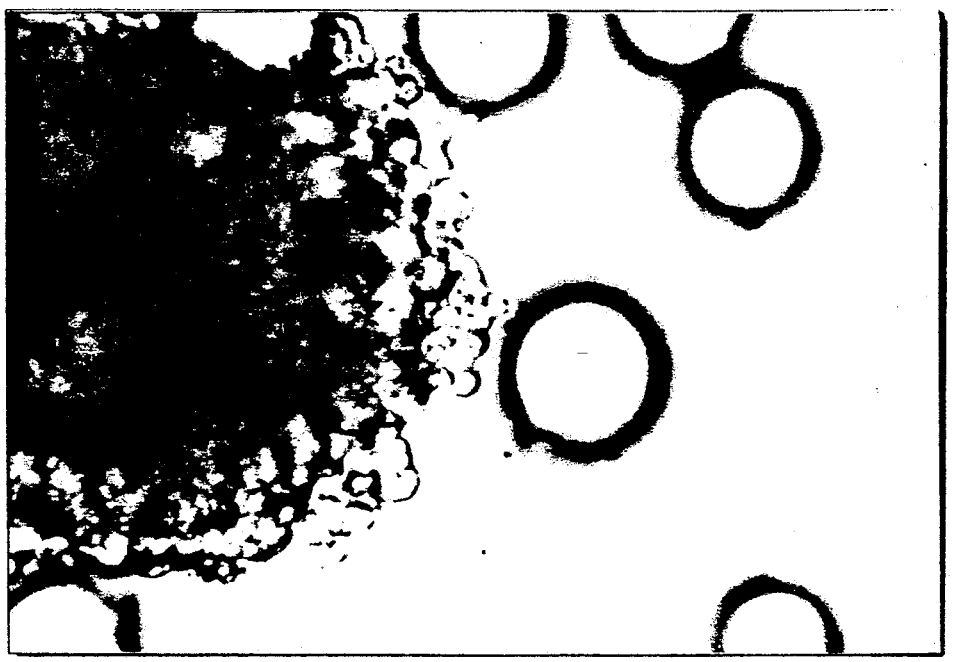
FIG. 8 is a micrograph of the morphology of aggregates of human kidney 293 cells according to the present invention.

During the cultivation period, cells formed aggregates. These aggregates settled to the bottom of the flask readily when agitation was stopped. When the glucose concentration was low in the medium, these aggregates were allowed to settle to the bottom and 50 ml of the medium were withdrawn and replaced with fresh medium. The concentration of free cells in the suspension was always below $1 \times 10^5$ cells/ml during the cultivation period. Shown in micrographs of FIG. 8 are the morphology of the aggregates of 293 cells.

Cell viability was very good even in large cell aggregates; however, the possibility exists of an artifact due to the possible limitation of diffusion of EtBR into the cell aggregates. To exclude this possibility, samples of the aggregates were exposed to trypsin solution (0.25% trypsin in PBS) for 15 min before they were exposed to mild pipetting. The trypsin treatment caused cells in the aggregates to dissociate and became a single cell suspension. These cells were stained with 0.1% trypan blue solution in PBS. Using this staining technique the dead cells are revealed by blue color due to their permeability to the dye. The viability of the cells after the trypsinization and the dissociation of the aggregates was more than 95%. The results thus demonstrate that 293 cells can be cultivated on microspheres of less than about 60 μm in an aggregate form to a very high cell density and retain viability in these aggregates.

EXAMPLE 3

Figure 9:
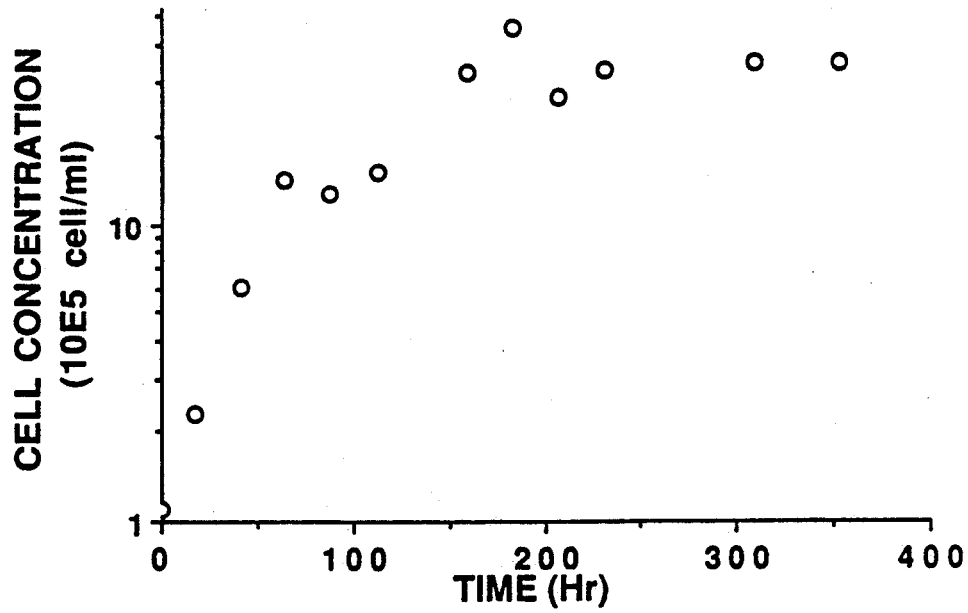
FIG. 9 is a graph of cell concentration vs. time for microsphere induced aggregate culture of swine testicular cells.
Figure 10:
FIG. 10 is a micrograph of the morphology of swine testicular cell aggregates grown according to the present invention.
Figure 14:
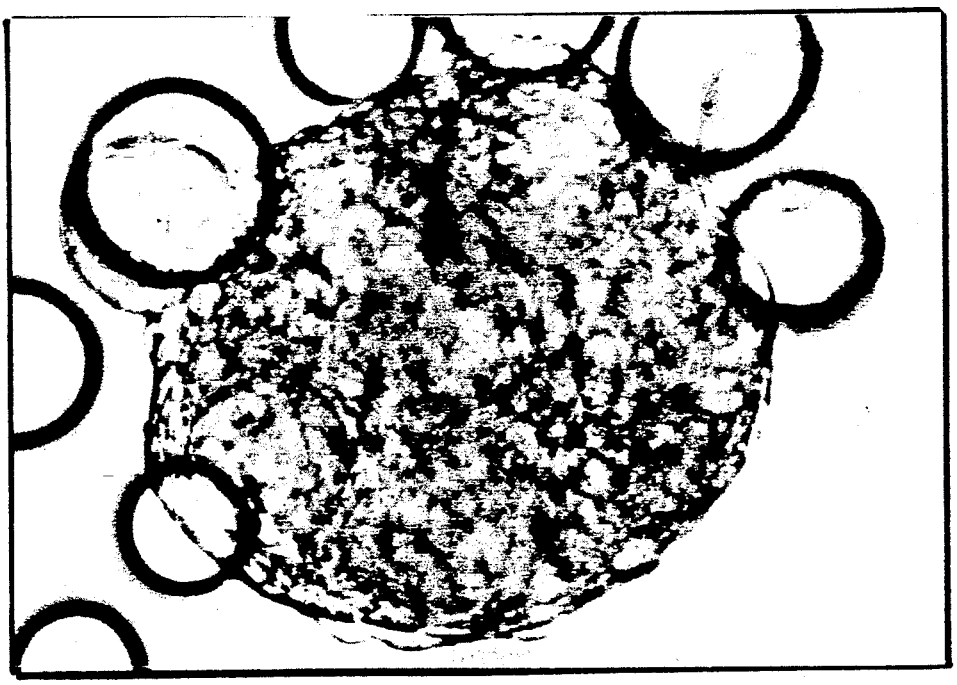
FIG. 14 is a micrograph of the aggregate of monkey kidney cells, Vero, grown according to the present invention.

Cultivation of Swine Testicular, ST Cell in Microsphere-Induced Aggregate Culture Swine testicular (ST) cells are diploid cells which grow as a monolayer on tissue culture flasks and on conventional microcarriers. They are not known to grow in aggregate form. They also do not grow in suspension. The cultivation was carried out in 250 ml spinner flask with 100 ml of microsphere stock suspension prepared as above at 0.5 g/l. Cells trypsinized from T-flasks were inoculated into the culture at $1.1 \times 10^5$ cells/ml. The medium used was DME/F12 3:1 supplemented with 5% FBS, 100 unit/ml penicillin G and 100 μg/ml streptomycin sulfate. After inoculation, cells attached to the microspheres readily and in 25-50 h aggregates were formed. Cell concentration continued to increase and the medium was replenished at 98 and 207 h. The final cell concentration reached after 230 h was approximately $3.3 \times 10^6$ cells/ml (FIG. 9). The micrographs of FIG. 10 show the morphology of cells grown as aggregates on microspheres of less than about 60 μm.

EXAMPLE 4

Cultivation of Monkey Kidney Cells, Vero, in Microsphere-Induced Aggregate Culture Vero is a continuous cell line which is strictly anchorage-dependent but does not exhibit contact inhibition and can grow up to a few layers of cells on tissue culture flasks. This cell line is available from American Type Culture Collection (Rockville, Md.). The cultivation conditions were the same as those described in the previous examples, except the agitation rate used was 70 rpm and the medium used was DMEM supplemented with 5% FBS.

Figure 11:
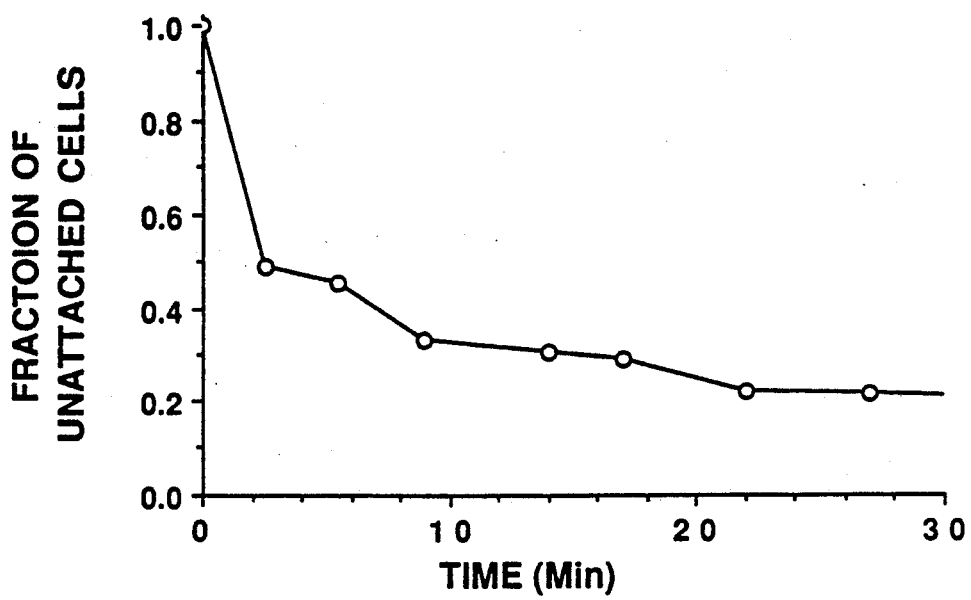
FIG. 11 shows the attachment kinetics of monkey kidney cells, Vero, to microspheres according to the present invention.

Cells grew to confluence on a T-75 flask, then were trypsinized and inoculated at $2.15 \times 10^5$ cells/ml with microsphere solution prepared as above. As cells attached to the microspheres, the free cells in the suspension disappeared. In the initial 7 h, the agitation was stopped periodically for 30 sec to allow for sediment of microspheres. During this 30-second period, a clear zone without microspheres appeared at the top of the culture fluid. A small sample was withdrawn from this microsphere-free zone and the number of free suspension cells were measured using a Coulter channelyzer attached to a Coulter counter, as described above. The disappearance of the free suspending cells is an indication of the attachment of cells to microspheres. FIG. 11 shows the attachment kinetics of Vero cells to microspheres; 90% of the cells attach within half an hour after inoculation. The remaining 20% attached at a much slower rate. By the end of the 7 h period, only the background level of particle count could be obtained in the suspension (data not shown).

Figure 12:
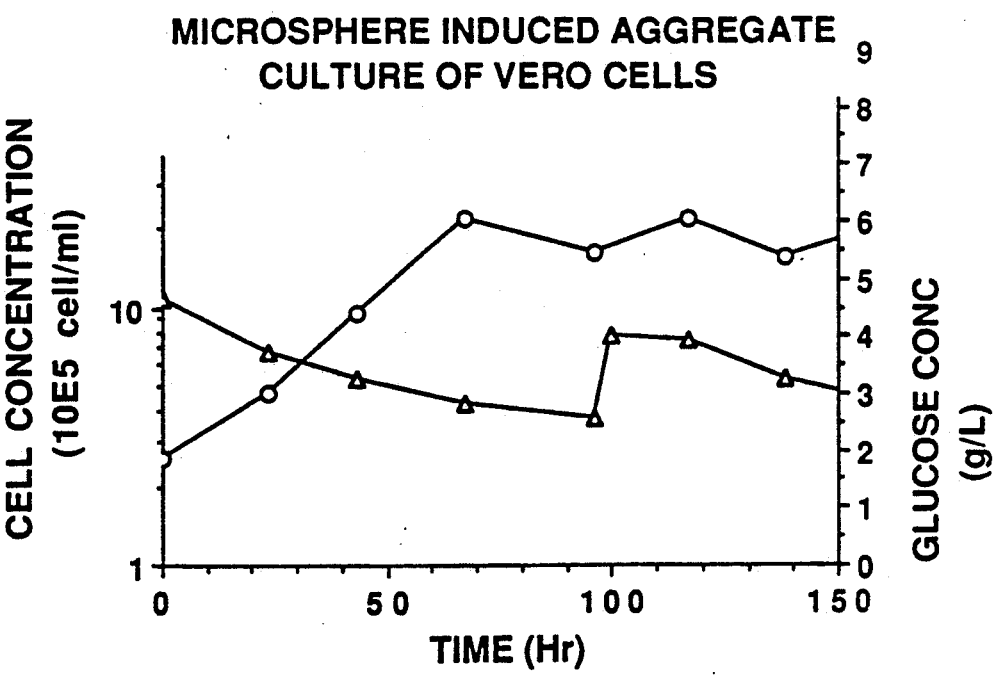
FIG. 12 shows the kinetics of cell growth and glucose consumption of monkey kidney cells, Vero, grown according to the present invention.

In a separate experiment, Vero cells were inoculated at $2.6 \times 10^5$ cells/ml with microsphere solution prepared as above and the kinetics of cell growth and glucose consumption are shown in FIG. 12. At 100 h, 50% of the medium was replenished. Cell concentration reached approximately $2 \times 10^6$ cells after approximately 100 h of cultivation. The microspheres used constituted less than 1% of the volume of the culture. Using conventional microcarriers such as Cytodex 1 (Sigma Chemical Co., St. Louis, Mo.), with an average diameter of 180 μm DEAE derivatized dextran beads, or polystyrene beads (SoloHill, MI) with an average diameter of 150–210 μm, an equivalent of approximately 6–8% settled volume of beads are required to achieve the same level of cell concentration.

Figure 13:
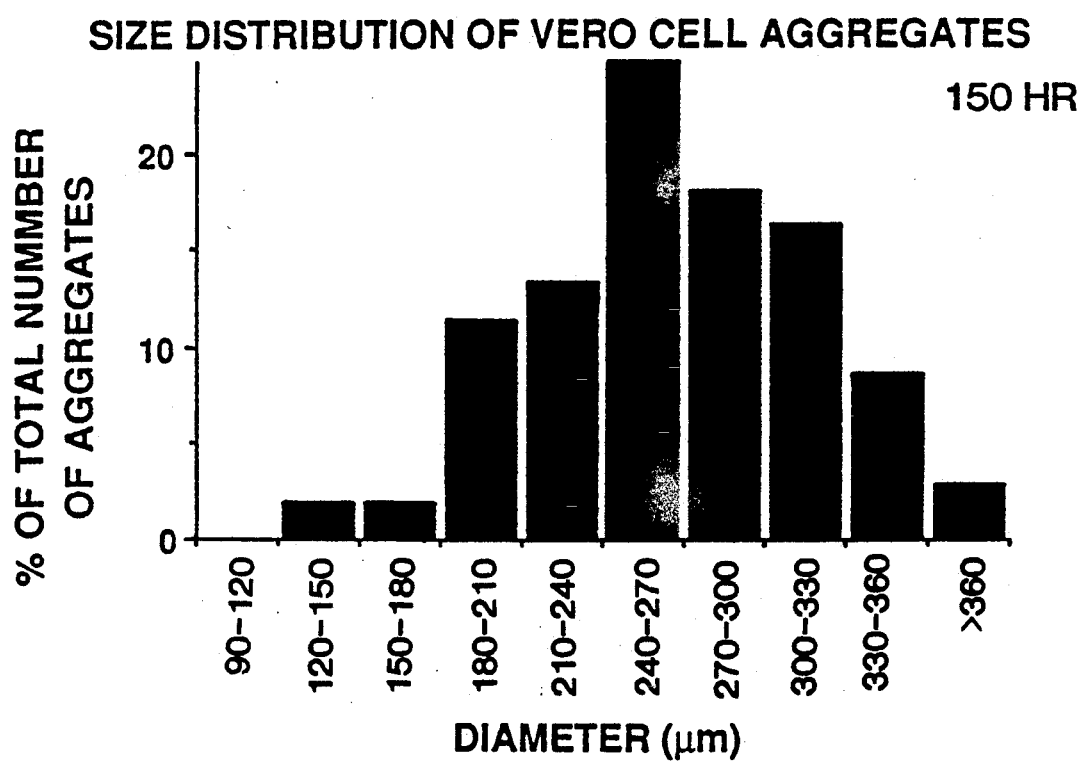
FIG. 13 is a histogram of size distribution of monkey kidney cells, Vero, grown according to the present invention.

At the end of cultivation, samples were taken for microscopic examination. The micrographs of these cell aggregates were taken and their diameter was measured. A histogram of size distribution of these aggregates is shown in FIG. 13. The medium aggregate diameter is approximately 250 μm. Shown in FIG. 15 is a micrograph of the aggregate obtained at the end of cultivation. A very high level of viability was attained, as indicated by the FDA/EtBr stain technique described previously.

By using microspheres of a hydrated derivatized diameter of less than about 60 μm, we have developed a new cultivation method to cultivate cells which have been known to be able to grow either as aggregates or in suspension, such as CHO and 293 cells, as well as cells which are strictly anchorage-dependent, such as Vero and ST cells. In the four examples presented above, a very low concentration (0.5 g/l) of microspheres of very small hydrated, derivatized diameter of less than about 60 μm was used. This amount of microcarrier constitutes only less than 1% of the culture volume. In all cases, a very high cell concentration was reached because cells are grown in an aggregate form. To achieve a similar cell concentration using conventional larger diameter microcarrier culture technology, a large amount of microcarrier would have to be used and the volume fraction of microcarriers will be in the range of 10% or even higher.

Viability observed in our microsphere-induced aggregates using microspheres of hydrated, derivatized diameter of less than about 60 μm is very high, as determined by FDA/EtBr stain as well as by dissociation of cells from the aggregate. In the case of Vero and ST cells, the cells do not spread out after attachment to the microsphere as they typically do when cultivated on conventional microcarriers or tissue culture flasks. Instead, they grow in a more spherical form and eventually form a tightly packed cell mass. The number of cell layers achieved in this aggregate was not determined due to the technical difficulty, but an estimation from the size of aggregates indicates that the range of the number of cells layers is in the vicinity of 10 to 20 from the surface to the center of the aggregate.

That which is claimed is:

1. A method of inducing aggregate formation of anchorage-dependent cells comprising the steps of:
   (a) forming a suspension of anchorage-dependent cells in nutrient medium; and
   (b) introducing into the suspension microspheres having a positive finite derivatized diameter of less than about 60 μm, when measured in a buffer saline or cell culture media.

2. A method of inducing aggregate formation of cells which grow in suspension or on surface comprising the steps of:
   (a) forming a uniform nutrient medium dispersion of cells which grow in suspension or on surface; and
   (b) introducing into the dispersion microspheres having a positive finite derivatized diameter of less than about 60 μm, when measured in a suitable buffer saline or cell culture media.

3. In a method of inducing aggregate formation of anchorage-dependent cells in a nutrient medium suspension of said anchorage-dependent cells, the improvement comprising introducing into said suspension microspheres of a positive finite derivatized diameter of less than about 60 μm, when measured in a suitable buffer saline or cell culture media.

4. In a method of inducing aggregate formation of suspension-grown or surface-grown cells in a uniform nutrient medium dispersion of said suspension-grown or surface-grown cells, the improvement comprising introducing into said dispersion microspheres of a positive finite derivatized diameter of less than about 60 μm, when measured in a suitable buffer saline or cell culture media.

5. A method according to claim 1, wherein the microspheres are of a diameter of approximately 15 to 25 μm.

6. A method according to claim 2, wherein the microspheres are of a diameter of approximately 15 to 25 μm.

7. The improvement according to claim 3, wherein the microspheres are of a diameter of approximately 15 to 25 μm.

8. The improvement according to claim 4, wherein the microspheres are of a diameter of approximately 15 to 25 μm.

9. A method according to claim 2, wherein the cells are selected from Chinese hamster ovary cells or human kidney cells 293.

10. A method according to claim 1, wherein the cells are selected from swine testicular cells or monkey kidney cells, Vero.

11. The improvement according to claim 3, wherein the cells are selected from swine testicular cells or monkey kidney cells, Vero.

12. The improvement according to claim 4, wherein the cells are selected from Chinese hamster ovary cells or human kidney cells 293.

13. A method according to claim 1, wherein the microspheres are able to accommodate a monolayer cell density of 10 to 20 cells per microsphere.

14. A method according to claim 2, wherein the microspheres are able to accommodate a monolayer cell density of 10 to 20 cells per microsphere.

15. The improvement according to claim 3, wherein the microspheres are able to accommodate a monolayer cell density of 10 to 20 cells per microsphere.

16. A method according to claim 1, wherein the microsphere concentration in the suspension formed by step (b) is approximately 0.5 g/l.

17. A method according to claim 2, wherein the microsphere concentration in the suspension formed by step (b) is approximately 0.5 g/l.

18. The improvement according to claim 3, wherein the microsphere concentration in the suspension formed by step (b) is approximately 0.5 g/l.

19. The improvement according to claim 4, wherein the microsphere concentration in the suspension formed by step (b) is approximately 0.5 g/l.

20. A method of inducing aggregate formation of animal cells comprising the steps of:
   (a) forming a suspension of animal cells in nutrient medium; and
   (b) introducing into the suspension microspheres of a positive finite derivatized diameter of not more than about 60 μm, when measured in a suitable buffer saline or cell culture media.

21. In a method of inducing aggregate formation of animal cells in a nutrient medium suspension of said animal cells, the improvement comprising introducing into said suspension microspheres of a positive finite derivatized diameter of not more than about 60 μm, when measured in a suitable buffer saline or cell culture media.

22. A method of inducing aggregate formation of animal cells by introducing into a nutrient medium suspension of animal cells microspheres of a positive finite derivatized diameter of not more than about 60 μm, when measured in a suitable buffer saline or cell culture media.

23. In a method of inducing aggregate formation of animal cells, the improvement comprising introducing into a suspension of animal cell sin nutrient medium microspheres of a positive finite derivatized diameter of not more than about 60 μm, when measured in a suitable buffer saline or cell culture media.

24. A method according to claim 1, wherein the microspheres are formed of dextran, gelatin, polyacrylamide-copolymerized with collagen or gelatin, polyacrylamide with modified charge, polystyrene or glass.

25. A method according to claim 2, wherein the microspheres are formed of dextran, gelatin, polyacrylamide-copolymerized with collagen or gelatin, polyacrylamide with modified charge, polystyrene or glass.

26. The improvement according to claim 3, wherein the microspheres are formed of dextran, gelatin, polyacrylamide-copolymerized with collagen or gelatin, polyacrylamide with modified charge, polystyrene or glass.

27. The improvement according to claim 4, wherein the microspheres are formed of dextran, gelatin, polyacrylamide-copolymerized with collagen or gelatin, polyacrylamide with modified charge, polystyrene or glass.

28. In a method of growing anchorage dependent cells in suspension, the improvement comprising employing in the suspension as a microcarrier support for attachment of cells, microspheres of a positive finite derivatized diameter of less than about 60 μm, when measured in a suitable buffer saline or cell culture media.

29. A method according to claim 1, in which the microsphere diameter is chosen so that a mean of cells/microsphere at initiation of culture is at least approximately 4 to 5 cells/microsphere and so that rate of cell attachment to microsphere surface at initiation of culture exhibits zero order kinetics with respect to surface area.

30. A method according to claim 2, in which the microsphere diameter is chosen sot hat at initiation of culture a mean of cells/microsphere is approximately 4 to 5 cells/microsphere and so that at initiation of culture rate of cell attachment to microsphere surface exhibits zero order kinetics with respect to surface area.

31. A method according to claim 3, in which the diameter of the microsphere is chosen so that a mean of cells/microsphere at initiation of culture is approximately 4 to 5 cells/microsphere and so that rate of cell attachment to microsphere surface at imitation of culture exhibits zero order kinetics with respect to surface area.

32. A method according to claim 4, in which the diameter of the microsphere is chosen sot at a mean of cells/microsphere at initiation of culture is approximately 4 to 5 cells/microsphere and so that rate of cell attachment to microsphere surface at initiation of culture exhibits zero order kinetics with respect to surface area.

33. A method according to claim 20, in which the diameter of the microsphere is chosen sot hat a mean of cells/microsphere at initiation of culture is approximately 4 to 5 cells/microsphere and so that rate of cell attachment to microsphere surface at initiation of culture exhibits zero order kinetics with respect to surface area.

34. A method according to claim 21, in which the diameter of the microsphere is chosen so that a mean of cells/microsphere at initiation of culture is approximately 4 to 5 cells/microsphere and so that rate of cell attachment to microsphere surface at initiation of culture exhibits zero order kinetics with respect to surface area.

35. A method according to claim 22, in which the diameter of the microsphere is chosen so that a mean of cells/microsphere at initiation of culture is approximately 4 to 5 cells/microsphere and so that rate of cell attachment to microsphere surface at initiation of culture exhibits zero order kinetics with respect to surface area.

36. A method according to claim 23, in which the diameter of the microsphere is chosen so that a mean of cells/microsphere at initiation of culture is approximately 4 to 5 cells/microsphere and so that rate of cell attachment to microsphere surface exhibits zero order kinetics with respect to surface area.

37. A method according to claim 28, in which the diameter of the microsphere is chosen so that a mean of cells/microsphere at initiation of culture is approximately 4 to 5 cells/microsphere and so that rate of cell attachment to microsphere surface at initiation of culture exhibits zero order kinetics with respect to surface area.

38. A method according to claim 1, wherein the diameter of the microspheres is a minimum of about 10 μm.

39. A method according to claim 2, wherein the diameter of the microspheres is a minimum of about 10 μm.

40. A method according to claim 3, wherein the diameter of the microspheres is a minimum of about 10 μm.

41. A method according to claim 4, wherein the diameter of the microspheres is a minimum of about 10 μm.

42. A method according to claim 20, wherein the diameter of the microspheres is a minimum of about 10 μm.

43. A method according to claim 21, wherein the diameter of the microspheres is a minimum of about 10 μm.

44. A method according to claim 22, wherein the diameter of the microspheres is a minimum of about 10 μm.

45. A method according to claim 23, wherein the diameter of the microspheres is a minimum of about 10 μm.

46. A method according to claim 28, wherein the diameter of the microspheres is a minimum of about 10 μm.

* * * * *

UNITED STATES PATENT AND TRADEMARK OFFICE
CERTIFICATE OF CORRECTION

PATENT NO. : 5,114,855

DATED : May 19, 1992

INVENTOR(S) : Wei-Shou Hu, and Stephane Goetghebeur

It is certified that error appears in the above-identified patent and that said Letters Patent is hereby corrected as shown below:

On the Title page, item [56], Other Publications, insert the following:

Hu, W.S. and Wang, D.I.C. (1987). Selection of Microcarrier Diameter for the Cultivation of Mammalian Cells on Microcarriers. Biotechnology and Bioengineering 30: 548-557.

Kubota, H. and Nagaiko, K. (1989). Cell Culture Using Microcarriers: The Effect of Chemical and Physical Properties of Microcarrier on Cell Attachment, Spreading and Growth. Abstract and presentation at the Japanese Associate of Animal Cell Technology Annual Meeting. Tsubuka City, Japan, November 20-22, 1989.

Page 1, col. 2, line 27+: citation of Karkare, et al. should be included with Other Publications.

Page 2, col. 2, line 3, "Biotechnical" should read --Biotechnology--.
Col. 3, line 15, "ben" should read --been--.
Col.13, line 18, "cell sin" should read --cells in--.
Col. 13, line 55, "sot hat" should read --so that--.
Col. 13, line 64, "imitation" should read --initiation--.
Col. 13, line 68, "sot at" should read --so that--.

UNITED STATES PATENT AND TRADEMARK OFFICE
CERTIFICATE OF CORRECTION

PATENT NO. : 5,114,855

DATED : May 19, 1992

INVENTOR(S) : Wei-Shou Hu, and Stephane Goetghebeur

It is certified that error appears in the above-identified patent and that said Letters Patent is hereby corrected as shown below:

Col. 14, line 7, "sot hat" should read --so that--.

Signed and Sealed this

Tenth Day of August, 1993

Attest:

MICHAEL K. KIRK

*Attesting Officer*  *Acting Commissioner of Patents and Trademarks*